US00H002084H

(19) United States

(12) Statutory Invention Registration (10) Reg. No.: US H2084 H

Picciolo et al. (43) Published: Oct. 7, 2003

(54) PENTACENE DERIVATIVES AS RED EMITTERS IN ORGANIC LIGHT EMITTING DEVICES

(75) Inventors: Lisa Crisafulli Picciolo, Silver Spring, MD (US); Hideyuki Murata, Alexandria, VA (US); Zakya H. Kafafi, Alexandria, VA (US)

(73) Assignee: The United States of America as represented by the Secretary of the Navy, Washington, DC (US)

(21) Appl. No.: 09/464,090

(22) Filed: Dec. 16, 1999

(51) Int. Cl.[7] ..... B32B 19/00; H01J 1/62

(52) U.S. Cl. ..... 428/690; 428/917; 313/504; 313/506

(58) Field of Search ..... 428/690, 917; 313/504, 506; 252/301.16

(56) References Cited

U.S. PATENT DOCUMENTS

| | | | | |
|---|---|---|---|---|
| 3,172,862 A | | 3/1965 | Gurnee et al. | 252/301.3 |
| 3,173,050 A | | 3/1965 | Gurnee et al. | 313/108 |
| 4,356,429 A | | 10/1982 | Tang | 313/503 |
| 5,281,489 A | * | 1/1994 | Mori et al. | 428/690 |
| 5,409,783 A | | 4/1995 | Tang et al. | 428/690 |
| 5,747,183 A | | 5/1998 | Shi et al. | 428/690 |
| 5,908,581 A | | 6/1999 | Chen et al. | 252/301.16 |
| 5,935,720 A | | 8/1999 | Chen et al. | 428/690 |
| 5,935,721 A | | 8/1999 | Shi et al. | 428/690 |
| 5,989,737 A | | 11/1999 | Xie et al. | 428/690 |
| 6,165,383 A | * | 12/2000 | Chou | 252/301.16 |
| 6,203,933 B1 | * | 3/2001 | Nakaya et al. | 428/690 |

FOREIGN PATENT DOCUMENTS

| | | |
|---|---|---|
| DE | 1 910 630 | * 10/1970 |
| JP | 8-311442 | * 11/1996 |

OTHER PUBLICATIONS

Maulding et al "Electronic Absorption and Fluorescence of Phenylethynyl–Substituted Acenes" Journal of Organic Chemistry, vol. 34, No. 6, Jun. 1969, pp. 1734–1736.

C. Burgdorff, T. Kircher and H.G. Lohmannsroben, "Photophysical Properties of Tetracene Derivatives in Solution" Spectrochim. Acto, 44A, (1988) pp. 1137–1141. (no month).

Shoustikov et al, "Electroluminescence Color Tuning by Dye Doping in Organic Light–Emitting Diodes", IEEE Journal of Selected Topics in Quantum Electronics, vol. 4, No. 1 Jan./Feb. 1998, pp. 3–13.

C.W. Tang et al "Electroluminescence of Doped Organic Thin Films", J. Appl. Phys. 65(9), May 1969, pp. 3610–3616.

C.W. Tang, "Organic Electroluminescent Materials and Devices" Information Display, Oct. 1996, pp. 16–19.

C.W. Tang and S.A. VanSlyke, "Organic Electroluminescent Diodes", Appl. Phys. Lett. 51(12), Sep. 21, 1987, pp. 913–915.

* cited by examiner

*Primary Examiner*—Michael J. Carone
*Assistant Examiner*—Aileen B. Felton
(74) *Attorney, Agent, or Firm*—John J. Karasek; Philip E. Ketner

(57) ABSTRACT

Pentacene derivatives substituted with two or more aromatic, substituted aromatic, heteroaromatic, or substituted heteroaromatic groups are dopants for organic electroluminescent devices. When combined with host materials and incorporated into an organic light emitting devices, the pentacene derivatives are red emitters with narrow spectra.

1 Claim, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PENTACENE DERIVATIVES AS RED EMITTERS IN ORGANIC LIGHT EMITTING DEVICES

BACKGROUND OF THE INVENTION

1. Field of the Invention

The present invention relates to red-emitting organic electroluminescent materials and devices in general and in particular to compositions and devices comprising host materials doped with pentacene derivatives.

2. Description of the Related Art

Organic electroluminescent devices have been the subject of considerable research because of their potential applications in a wide variety of flat panel displays, especially ultra thin flat panel displays. Organic electroluminescent devices are very competitive with liquid crystal displays because of their very bright self-emission, low power consumption, low cost of organic materials, ease of color tunability and processability. The present technology will be competing with liquid crystal displays, which are replacing cathode ray tubes as a means of displaying visual information.

One effective approach for achieving color tunability in OLEDs, as well as improving device efficiency and durability, is by doping of fluorescent materials into organic host materials. Organic electroluminescent devices that include organic host materials and dopants are disclosed, for example, in the following patents and publications incorporated herein by reference: U.S. Pat. No. 3,172,862 to Gurnee et al; U.S. Pat. No. 3,173,050 to Gurnee; U.S. Pat. No. 3,710,167 to Dresner et al; U.S. Pat. No. 4,356,429 to Tang; U.S. Pat. No. 4,769,292 to Tang et al; U.S. Pat. No. 5,059,863 to Toshiro et al; U.S. Pat. No. 5,126,214 to Tokailin et al; U.S. Pat. No. 5,382,477 to Saito et al; U.S. Pat. No. 5,409,783 to Tang et al; U.S. Pat. No. 5,554,450 to Shi et al; U.S. Pat. No. 5,635,307 to Takeuchi et al; U.S. Pat. No. 5,674,597 to Fujii et al; U.S. Pat. No. 5,709,959 to Adachi et al; U.S. Pat. No. 5,747,183 to Shi et al; U.S. Pat. No. 5,756,224 to Börner et al; U.S. Pat. No. 5,861,219 to Thompson et al; U.S. Pat. No. 5,908,581 to Chen et al; U.S. Pat. No. 5,932,363 to Hu et al; U.S. Pat. No. 5,935,720 to Chen et al; U.S. Pat. No. 5,935,721 to Shi et al; U.S. Pat. No. 5,948,941 to Tamano et al; U.S. Pat. No. 5,989,737 to Xie et al; International Publication No. WO 98/06242 (Forrest et al); C. W. Tang et al "Electroluminescence of Doped Organic Thin Films", J. Appl. Phys. 65(9), May 1969, pp 3610–3616; C. W. Tang and S. A. VanSlyke, "Organic Electroluminescent Diodes", Appl. Phys. Lett. 51(12), Sep. 21, 1987, pp. 913–915; C. W. Tang, "Organic Electroluminescent Materials and Devices" Information Display, Oct. 1996, pp. 16–19; J. Shi and C. W. Tang, "Doped Organic Electroluminescent Devices with Improved Stability", Appl. Phys. Lett 70(13) Mar. 31, 1997, pp. 1665–1667; Shoustikov et al, "Electroluminescence Color Tuning by Dye Doping in Organic Light-Emitting Diodes", IEEE Journal of Selected Topics in Quantum Electronics, Vol. 4, No. 1 Jan./Feb. 1998, pp 3–13; Baldo et al, "Highly Efficient Phosphorescent Emission from Organic Electroluminescent Devices", Nature, Vol.395, Sep. 10, 1998, pp 151—153; O'Brien et al "Improved Energy Transfer in Electrophosphorescent Devices", Applied Physics Letters, Vol. 74, No. 3, Jan. 18, 1999, pp. 442–444.

Full color electroluminescent displays require efficient red, green and blue electroluminescent materials. Currently, there is a need for more efficient red emitting materials, particularly for compounds with excellent color purity, chemical stability, including photochemical stability and electrochemical stability, high photoluminescence and electroluminescence quantum efficiencies and an extended device lifetime. U.S. Pat. No. 4,769,292 to Tang et al, U.S. Pat. No.5,908,581 to Chen et al; and U.S. Pat. No. 5,935,720 to Chen et al. describe compounds such as the DCM/DCJ class of red emitters (4-(dicyanomethylene)-2methyl-6-(p-dimethylaminostyryl)4H-pyran and julolidyl derivatives). These compounds typically exhibit broad emission spectra that reduce the red color purity at lower red wavelengths, giving them an orange hue. At higher red wavelengths, the broad emission band results in reduced luminance, since much of the emission is in the long wavelength region where the eye is less sensitive. Moreover, the synthesis of DCM/DCJ compounds results in a by-product that quenches fluorescence. The by-product is difficult to remove during purification and its presence reduces the electroluminescent efficiency of devices using the compounds. U.S. Pat. No. 5,409,783 to Tang et al describes a phthalocyanine compound that has a peak emission in the deep red wavelength region of 660 nm–780 nm. This compound, while useful for photographic printing processes, is less useful in display applications, since the eye has a low response to emission in these wavelengths.

SUMMARY OF THE INVENTION

It has now been discovered that pentacene derivatives exhibit very narrow emission spectra and produce a very pure red color in a region of the spectrum that is useful for display applications. When pentacene derivatives are doped into the active emissive layer of organic light-emitting devices, efficient energy transfer from the host material to the pentacene derivatives and/or carrier recombination on the pentacene derivatives takes place, resulting in red electroluminescence predominantly from the pentacene derivatives.

Accordingly, the present invention is directed to an electroluninescent composition comprising a host material and a red dopant, wherein the red dopant is a pentacene derivative substituted with two or more aromatic, substituted aromatic, heteroaromatic or substituted heteroaromatic groups.

Further, the present invention is directed to a heterostructured organic light emitting device for producing electroluminescence, the heterostructure having an emissive layer comprised of a host material and a red dopant, wherein the red dopant is a pentacene derivative substituted with two or more aromatic, substituted aromatic, heteroaromatic or substituted heteroaromatic groups.

The pentacene derivatives of the present invention have the advantages that they are relatively easy to synthesize and that the synthesis process does not produce a by-product that quenches fluorescence (which is a recurring problem in some fluorescent red dyes such as DCM/DCJ compounds). Moreover, the pentacene derivatives have narrow emission spectra in the red visible spectral region appropriate for display applications.

DETAILED DESCRIPTION OF THE PREFERRED EMBODIMENTS

Figure 1:
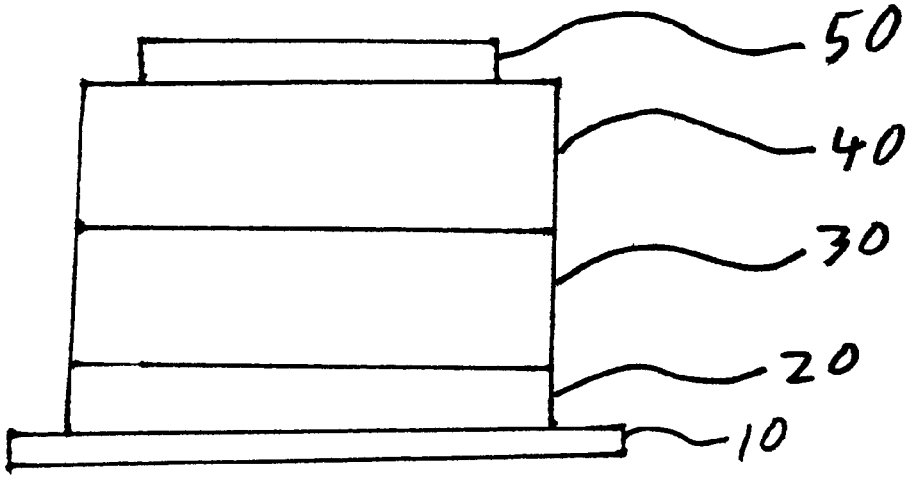
FIG. 1 is a cross-sectional representation of a first embodiment of an organic light emitting device of the present invention.

The materials of the present invention are red-emitting electroluminescent composites comprising host materials and red dopants, the red dopants being pentacene derivatives as described below.

The host material may be any compound or mixture of compounds typically used or capable of being used in the active emitting layer and/or carrier transporter of an electroluminescent device. Typically, the host material is a material that has good electron transport and/or hole transport properties, has good morphological properties so that it forms thin amorphous films by vacuum evaporation and has good electrochemical stability. The photoluminescence spectra of the host material should overlap with the absorption spectra of the guest material so that efficient F ürster/Dexter energy transfer takes place. The host material should not quench the emission from the guest material, should have a bandgap greater than the guest material so that carrier trapping can occur, should have a larger ionization potential than that of the guest material so that hole trapping can occur and should have a smaller electron affinity than that of the guest material so that electron trapping can occur.

Typical host materials include hole transport materials such as N,N'-diphenyl-N,N'-bis(3-methylphenyl)1,1'-biphenyl-4,4'diamine (TPD), N,N'-diphenyl-1,1'-biphenyl-4,4'-diamine (NPB), N,N,N,N '-tetrakis(4-methylphenyl)(1,1'-biphenyl)-4,4'diamine (TTB) and starburst compounds such as 4,4',4'-tris(1-naphthylphenylamino)triphenylamine (1-TNATA). Typical host materials also include electron transport materials such as metal chelate compounds such as tris(8-hydroxyquinolinato)aluminum ($ALQ_3$), tris(8-hydroxyquinolinato) gallium III ($Gaq_3$), tris-(4-methyl-8-hydroxyquinolinato) aluminum (III) ($Almq_3$), bis(10-hydroxybenzo[h]quinolinato) beryllium ($BeBq_2$), tris(4-phenanthridinolato) aluminum III ($Alph_3$), and bis(2-styryl-8-quinolinato) zinc II ($Znsq_2$). Also, typical electron transport materials include 1,3,4-oxadiazole derivatives such as 1,3,[5-(4-tert-butylphenyl)-1,3,4-oxadiazole-2-yl] benzene (OXD7), 2-(4-biphenylyl)-5-(4-tert-butylphenyl-oxadiazole (butyl-PBD), 1,2,4-triazoles (TAZs) and 5,5'-bis (dimesitylboryl)-2,2'-bithiophene (BMB-2T).

The pentacene derivatives of the present invention are compounds comprising a pentacene backbone substituted in two or more positions with aromatic groups, substituted aromatic groups, heteroaromatic groups and substituted heteroaromatic groups. In general, bulky or hindered substituents such as aromatic groups, substituted aromatic groups, heteroaromatic groups and substituted heteroaromatic groups on a pentacene derivative contribute to more efficient electroluminescence due to increase of photoluminescence by the reduction of the aggregation of individual molecules of the pentacene derivative. Further, heteroaromatic substituents or substituents that have longer conjugation may cause a red-shift of the spectra. Suitable heteroaromatic substituents include furyl, thienyl, pyridyl, oxazoly, isoxazoly, thiazoly, isothiazoly, pyridyl, pyridazyl, pyrimidyl and pyrazyl groups. Suitable groups with longer conjugation include styryl groups and styryl groups substituted with alkyl, phenyl, naphthyl, anthracenyl and biphenyl. Another reason for using aromatic and heteroaromatic substituents is that it has been shown that aromatic and heteroaromatic substituents attached to polycyclic aromatic hydrocarbons such as tetracene reduce intersystem crossing between singlet($S_1$) to triplet ($T_n$) states, resulting in higher photoluminescent efficiency. See, for example, C. Burgkorff, T. Dircher and H. G. Lohmannsroben, Spectrochim. Acto, 44A, 1137 (1988), incorporated herein by reference. The present inventors believe that similar principles would apply to pentacene derivatives and that this phenomenon would provide for greater efficiency in an electroluminescent device.

Pentacene derivatives of the present invention include, for example, compounds of the formula:

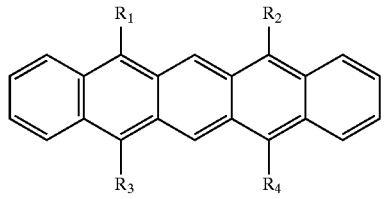

wherein $R_1$, $R_2$, $R_3$, and $R_4$ are independently aromatic, substituted aromatic, heteroaromatic or substituted heteroaromatic groups. Preferably, $R_1$, $R_2$, $R_3$ and $R_4$ are unsubstituted, alkyl-substituted or aryl-substituted phenyl, naphthyl, anthracenyl, biphenyl, furyl, thienyl, pyridyl, oxazoly, isoxazoly, thiazoly, isothiazoly, pyridyl, pyridazyl, pyrimidyl, or pyrazyl groups.

Pentacene derivatives of the present invention may also include, for example, compounds of the formula:

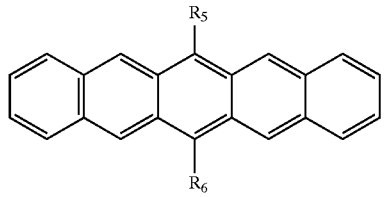

wherein $R_5$ and $R_6$ are independently aromatic, substituted aromatic, heteroaromatic or substituted heteroaromatic groups. Preferably, $R_5$ and $R_6$ are unsubstituted, alkyl-substituted or aryl-substituted phenyl, naphthyl, anthracenyl, biphenyl, furyl, thienyl, pyridyl, oxazoly, isoxazoly, thiazoly, isothiazoly, pyridyl, pyridazyl, pyrimidyl, or pyrazyl groups.

Pentacene derivatives may also include compounds of the following formulae:

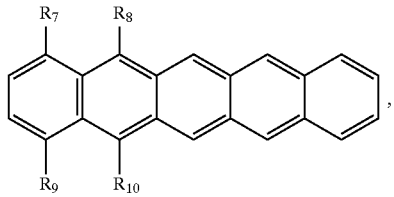

,

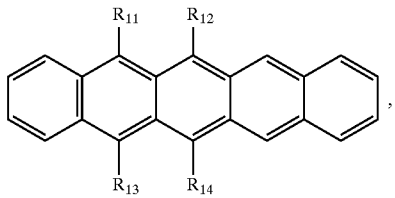

,

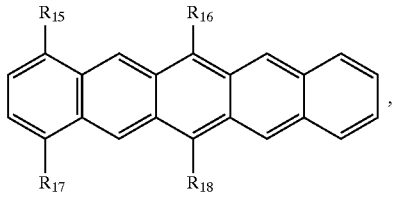

,

-continued

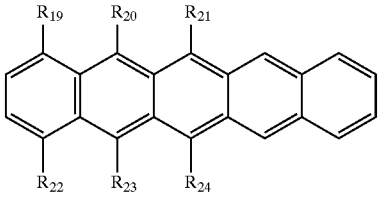

,

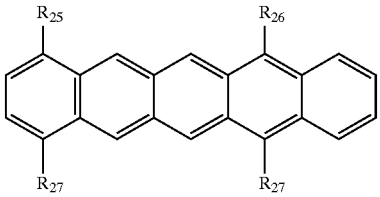

,

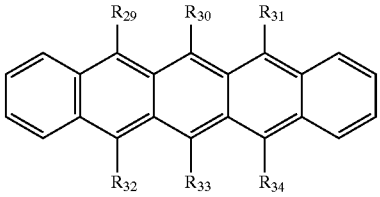

,

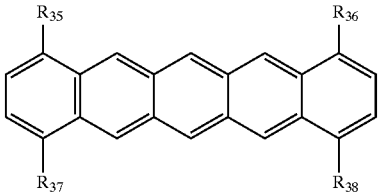

,

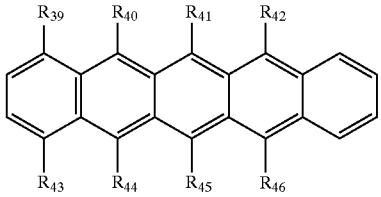

, and

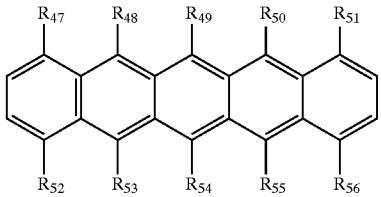

.

wherein $R_7$–$R_{56}$ are independently aromatic, substituted aromatic, heteroaromatic or substituted heteroaromatic groups and wherein preferably, $R_7$–$R_{56}$ are unsubstituted, alkyl-substituted or aryl-substituted. phenyl, naphthyl, anthracenyl, biphenyl, furyl, thienyl, pyridyl, oxazoly isoxazoly, thiazoly isothiazoly, pyridyl, pyridazyl, pyrimidyl, or pyrazyl groups.

The reason for providing a large number of pentacene derivatives in the present invention is to provide a large number of choices in terms of emission wavelengths within the red region. Each derivative is expected to have a slightly different electronic structure and a slightly different emission spectrum. Thus, with a large number of choices, a person skilled in the art may fine-tune an electroluminescent device by selecting a derivative that meets a particular emission requirement.

An example of a pentacene derivative that exhibits a very narrow emission within the desired range of the red spectrum is 6,13-diphenylpentacene.

The pentacene derivatives of the present invention may be synthesized by any method known in the art for attaching other aromatic or heteroaromatic groups to a polycyclic aromatic hydrocarbon. For example, the pentacene derivatives may be synthesized by starting with a pentacene quinone derivative, such as pentacene-5,7,12,14-tetraone or 6,13-pentacenequinone and then treating the pentacene quinone derivative with an excess of an organolithium compound containing the side group (RLi). In a typical synthesis, after the mixture is refluxed for four hours, it is acidified with an excess of aqueous acetic acid (AcOH) and stirred overnight at room temperature. The intermediate product, an alcohol, is isolated and reduced with an excess of tin chloride dihydrate ($SnCl_2.2H_2O$) dissolved in aqueous acetic acid at room temperature in the presence of nitrogen gas. Dilution with water precipitates the final pentacene derivative product. The general reaction may be illustrated by the following reaction scheme for creating a 6,13 di-substituted pentacene derivative:

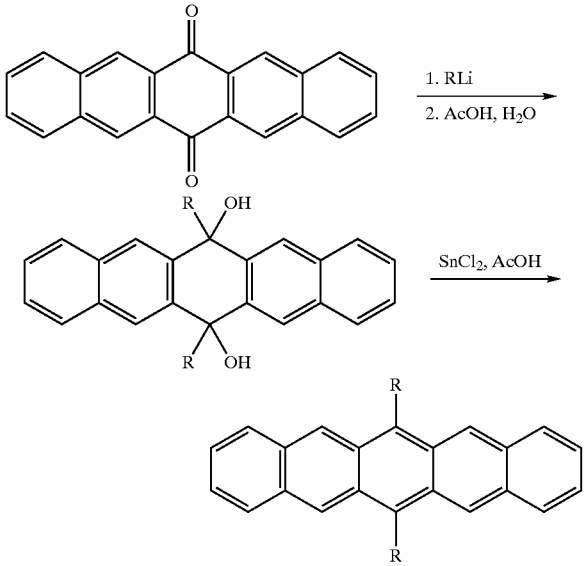

wherein R is the desired substituent. This method of attaching an R group to a polycyclic ring is described generally in the following publication incorporated herein by reference: Maulding et al "Electronic Absorption and Fluorescence of Phenylethynyl-Substituted Acenes" Journal of Organic Chemistry, Vol. 34, No. 6, Jun. 1969, pp 1734–1736.

The organic light emitting device of the present invention can have the same configuration as any host-dopant-containing electroluminescent device known in the art. A typical organic light emitting device, such as is described, for example, in U.S. Pat. No. 5,409,783 and other patents and publications referenced above, includes an anode separated from a cathode by an electroluminescent medium. The anode is typically a high work function, hole injecting material such as, for example indium tin oxide (ITO). The cathode is typically a low work function, electron-injecting material such as, for example, magnesium-silver alloy (Mg:Ag). The anode and the cathode are connected by conductors to an external power source, which can be a continuous direct current or alternating current voltage source or an intermittent current voltage source. Any convenient conventional power source, including any desired switching circuitry, can be employed which is capable of positively biasing the anode with respect to the cathode. Either the anode or cathode can be at ground potential.

The electroluminescent device can be viewed as a diode which is forward biased when the anode is at a higher potential than the cathode. Under these conditions, the anode injects holes (positive charge carriers), into the luminescent medium while the cathode injects electrons into the luminescent medium. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode, which eventually leads to hole-electron recombination within the organic luminescent medium. In a device that contains a host/dopant composition, the host receives the hole/electron recombination energy and then by Förster or Dexter (i.e. radiationless) energy transfer processes, transfers that excitation energy to the dopant compound, which in turn radiates to produce visible radiation in the desired wavelength. Reverse biasing of the electrodes interrupts charge injection, reverses the direction of mobile charge migration, and terminates light emission. The most common mode of operating the organic electroluminescent device is to employ a forward biasing DC power source and to rely on external current interruption or modulation to regulate light emission.

Figure 2:
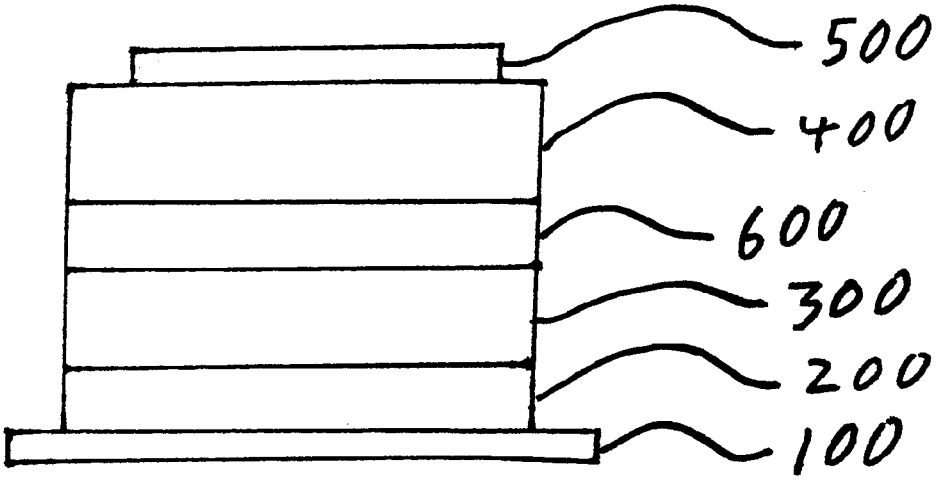
FIG. 2 is a cross-sectional representation of a second embodiment of an organic light emitting device of the present invention.

As used herein, the term "heterostructure" refers to a device having a layered structure including at least an anode, hole transporting layer, electron transporting layer and a cathode, as described above. In such a device, the host/dopant composition may be part of the hole transporting layer or the electron transporting layer. The term "heterostructure" also includes any variations on the basic device, such as a device having a separate emissive layer between the hole transport layer and the electron transport layer. Examples of devices of the present invention are illustrated in FIGS. 1 and 2. FIG. 1 depicts a device having a substrate 10 having deposited thereon successive layers of an anode 20, a hole transporting layer 30, an electron transporting layer 40 and a cathode 50. FIG. 2 depicts a device having a substrate 100 having deposited thereon successive layers of an anode 200, a hole transporting layer 300, and active emitting layer 600 and an electron transporting layer 400 and a cathode 500. Other configurations are possible, such as devices having separate layers for red, blue and green emitting material, as described, for example in International Publication No. WO 98/06242 (Forrest et al).

For the fabrication of the organic light emitting devices, pre-cleaned glass substrates patterned with indium tin oxide (ITO) stripes can be used. The hole transport layer, the emissive layer (if present as a separate layer) and the electron transport layer can be prepared by consecutive vapor deposition of each layer. Alternatively, the layers can be prepared from solution by spin casting or by other means of creating a thin film layer on a substrate. For films prepared by vapor deposition, the host/dopant composition, whether it be part of the hole transport layer, a separate emissive layer or the electron transport layer is formed by co-evaporation of the host material and the pentacene derivative. Typically, the vapor deposition is carried out in a vacuum chamber under a base pressure of $2\times10^{-7}$ Torr. A Mg:Ag alloy top layer is deposited through a shadow mask forming metal stripes perpendicular to the indium tin oxide stripes.

Photoluminescence and electroluminescence spectra are measured inside a glove box purged with dry nitrogen. The excitation laser beam for photoluminescence is brought into the glove box through an optical fiber. The luminescence is collected and brought out through another optical fiber. Voltage-current-luminance measurements are performed with a high current source and luminance meter. Device performance is evaluated based on the external quantum efficiency defined as the ratio of the number of emitted photons to the number of injected carriers.

Having described the invention, the following examples are given to illustrate specific applications of the invention, including the best mode now known to perform the invention. These specific examples are not intended to limit the scope of the invention described in this application.

EXAMPLE

Organic light emitting devices (OLEDs) were fabricated in high vacuum ($10^{-7}$ Torr) by sequentially depositing thin films of a hole transport layer, an active emissive layer, an electron transport layer followed by a metal film cathode (reflective) onto an indium tin oxide (transparent anode) patterned glass substrate. The active emissive layer consisted of a derivative of pentacene doped into a hole or an electron transport material that serves as the host. In the devices that were fabricated, 6,13-diphenylpentacene was used as the guest molecule, and N,N'-diphenyl-N,N'-bis(3-methylphenyl) 1,1'-biphenyl-4,4'diamine (TPD) or tris(8-hydroxyquinolinato)aluminum ($ALQ_3$) was used as the host.

The electroluminescence spectrum of a device where the active layer is 6,13-diphenylpentacene doped into $ALQ_3$ exhibits a very narrow emission peak in the visible red region centered at 625 nm. The CIE coordinates of the device are X=0.64, y=0.34. These coordinates lie within the desired range of the color gamut that is used for color television. A device wherein the active emissive layer consists of a host doped with an optimal concentration of 6,13-diphenylpentacene shows an electroluminescence quantum efficiency of 2.5% at 100 $A/m^2$. The efficiency for this unoptimized device structure is comparable to that of the best-published data to date for red OLEDs that use a porphine-based phosphor as the dopant in an optimized device structure. (see O'Brien et al "Improved Energy Transfer in Electrophosphorescent Devices", Applied Physics Letters, Vol. 74, No. 3, Jan. 18, 1999, pp. 442–444.)

Obviously, many modifications and variations of the present invention are possible in light of the above teachings. It is therefore to be understood that, within the scope of the appended claims, the invention may be practiced otherwise than as specifically described.

What is claimed is:

1. A compound of the formula:

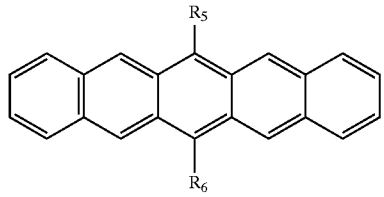

wherein $R_5$ and $R_6$ are phenyl groups.

* * * * *